United States Patent
Eaton et al.

[11] Patent Number: 6,159,584
[45] Date of Patent: Dec. 12, 2000

[54] ELASTIC TAB LAMINATE

[75] Inventors: Bradley W. Eaton, Woodbury; Nedlin B. Johnson, Minneapolis; Michael R. Gorman, Lake Elmo; Shou-Lu G. Wang, Woodbury, all of Minn.

[73] Assignee: 3M Innovative Properties Company, St. Paul, Minn.

[21] Appl. No.: 09/049,727

[22] Filed: Mar. 27, 1998

[51] Int. Cl.$^7$ .................................................. B32B 27/12

[52] U.S. Cl. ........................ 428/198; 442/328; 442/398; 442/399

[58] Field of Search .................................. 442/328, 398, 442/399; 428/198

[56] References Cited

U.S. PATENT DOCUMENTS

| | | | |
|---|---|---|---|
| 4,381,781 | 5/1983 | Sciaraffa et al. | 604/372 |
| 4,857,067 | 8/1989 | Wood et al. | 604/389 |
| 5,057,097 | 10/1991 | Gesp | 604/389 |
| 5,156,973 | 10/1992 | Shanbrom | 436/16 |
| 5,399,219 | 3/1995 | Roessler et al. | 156/259 |
| 5,540,796 | 7/1996 | Fries | 156/164 |
| 5,549,592 | 8/1996 | Fries et al. | 604/389 |
| 5,593,401 | 1/1997 | Sosalla et al. | 604/385.2 |
| 5,620,780 | 4/1997 | Krueger et al. | 428/179 |
| 5,669,897 | 9/1997 | Lavon et al. | 604/385.2 |

FOREIGN PATENT DOCUMENTS

| | | | |
|---|---|---|---|
| 0 191 355 | 8/1986 | European Pat. Off. | A41B 13/02 |
| 0 375 862 | 7/1990 | European Pat. Off. | C09J 7/02 |
| 0 704 196 | 4/1998 | European Pat. Off. | A61F 13/58 |
| 2 291 783 | 2/1996 | United Kingdom | A61F 13/15 |

Primary Examiner—Elizabeth M. Cole
Attorney, Agent, or Firm—Gary L. Griswold; Robert W. Sprague; Wiliam J. Bond

[57] ABSTRACT

There is provided an extensible elastic tab designed to be adhered to the edge of an article, formed using a coextruded elastic film comprising at least one elastic layer and at least one second layer on at least a first face of the elastic layer with at least one face of the coextruded elastic film attached to at least a partially extensible nonwoven layer. The partially expandable, or extensible nonwoven layer has at least one first portion with limited extensibility in a first direction and at least one second inextensible portion in the first direction. The extensible elastic tab when stretched to the extension limit of the first portion or portions in the first direction will elastically recover at least 1.0 cm, preferably at least 2 cm providing an elastic tab having a Useful Stretch Ratio (as defined in the Examples) of at least 30 percent. The Useful Stretch Ratio includes the portion of the elastic recovery length having an elastic recovery force of greater than 20 grams/cm force, but below a given extension which generally is 90 percent of the extension limit. Further the elastic tab in the region of the Useful Stretch Ratio preferably has an incremental extension force of less than about 300 grams/cm. The invention tab provides definable predictable elastic performance and is useful as a fastening tab used to join to surfaces requiring elastic engagement, particularly a person or animal. The tab is particularly useful as a diaper fastening tab.

53 Claims, 8 Drawing Sheets

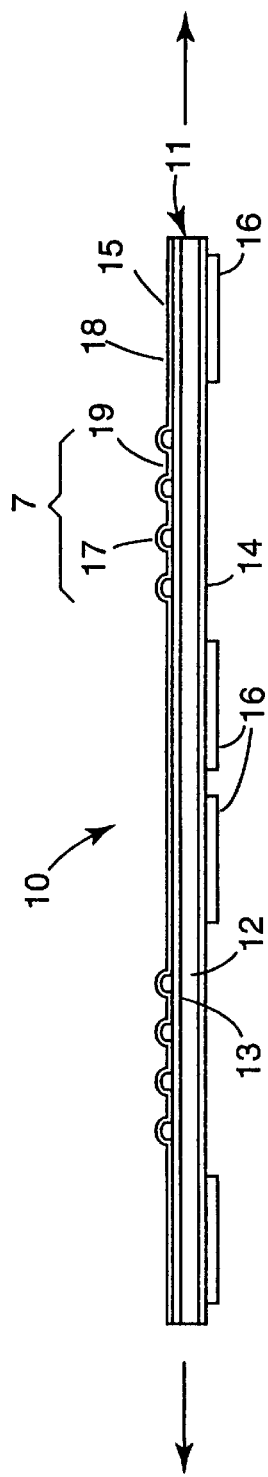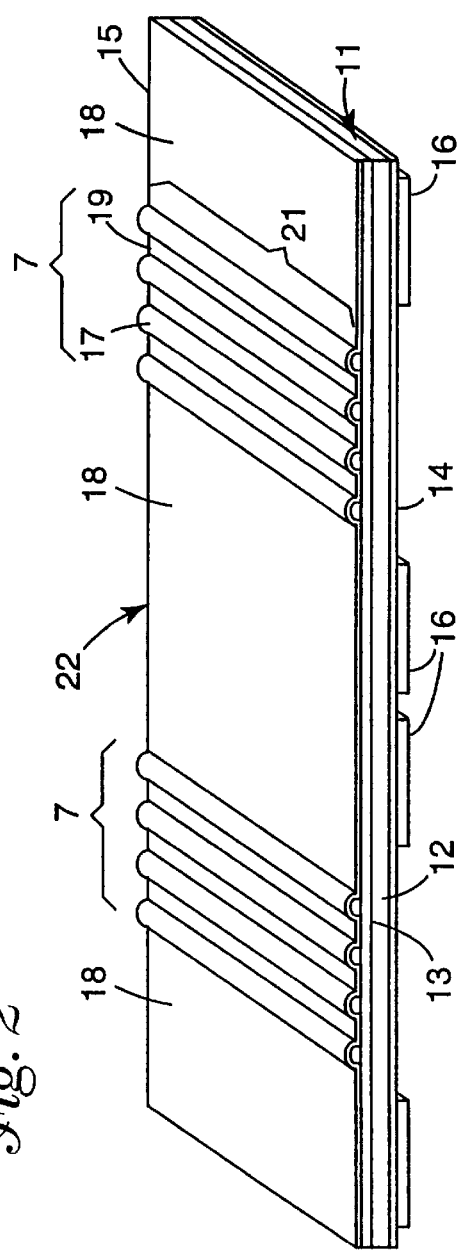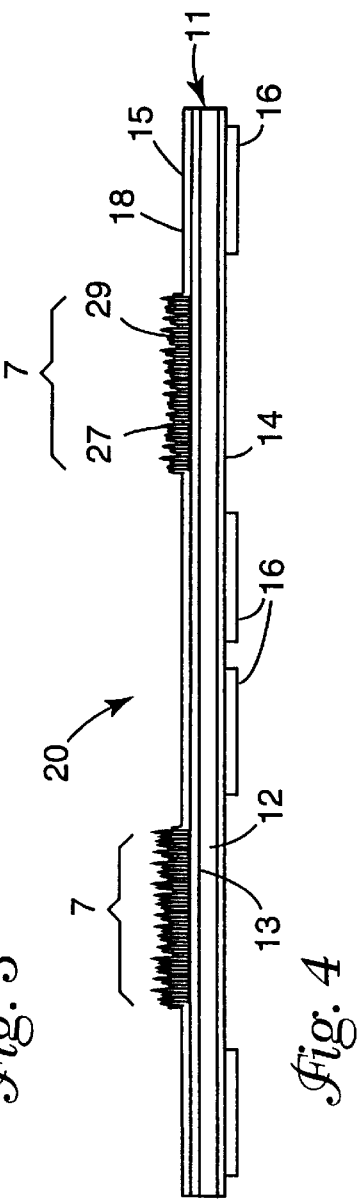

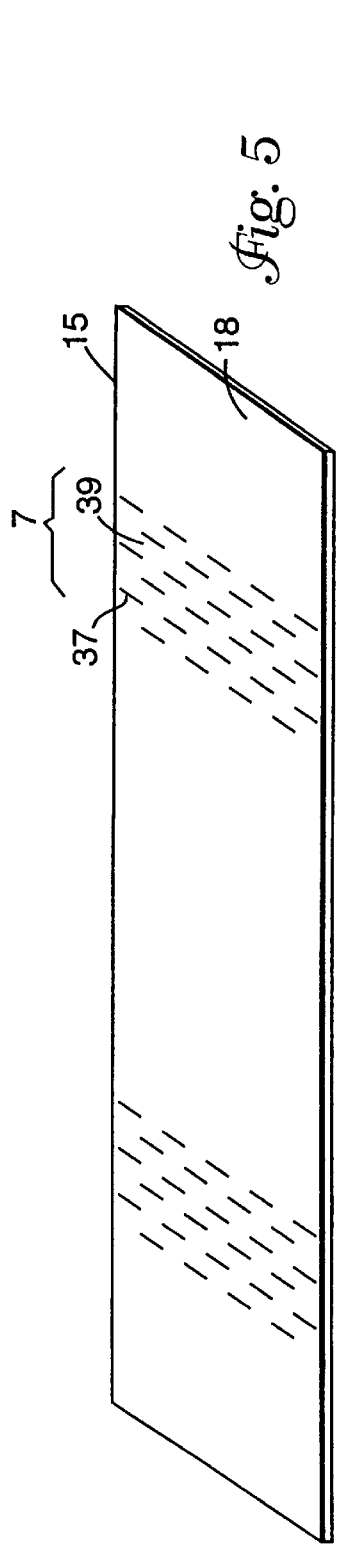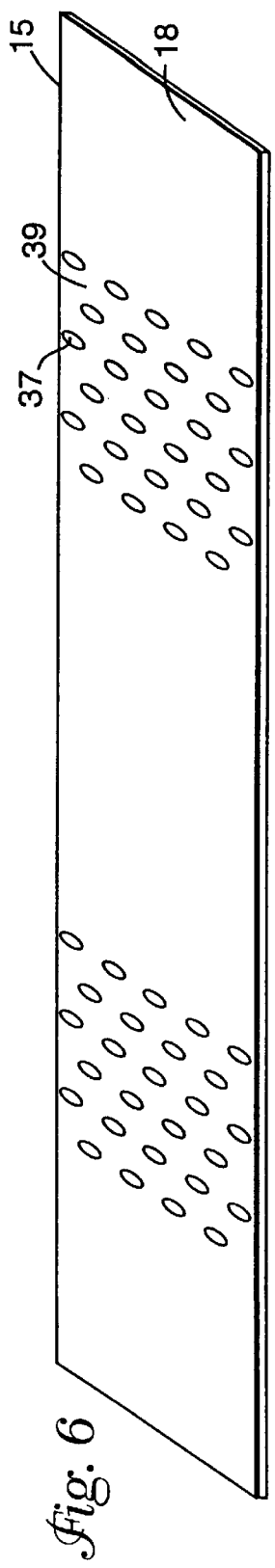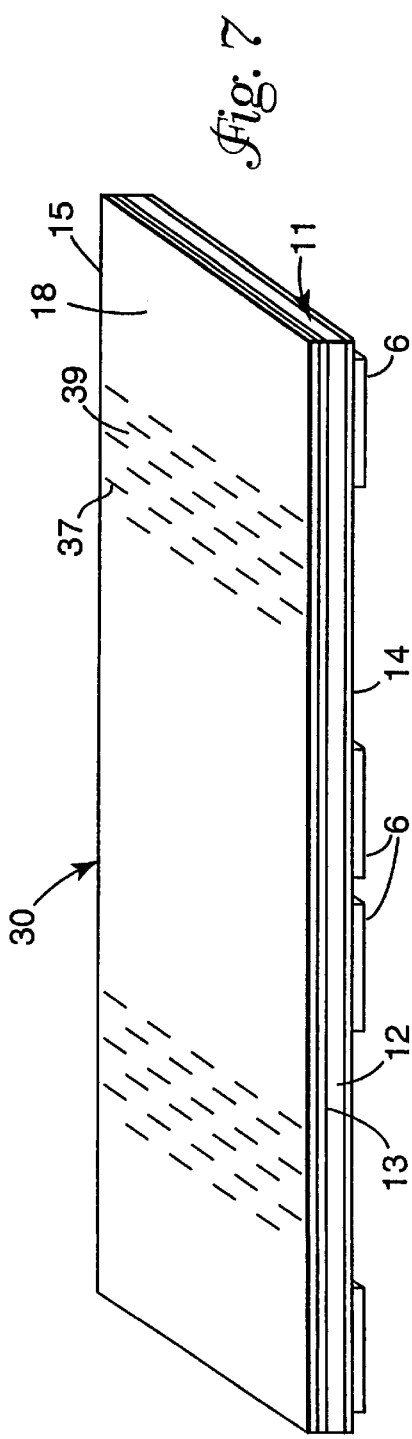

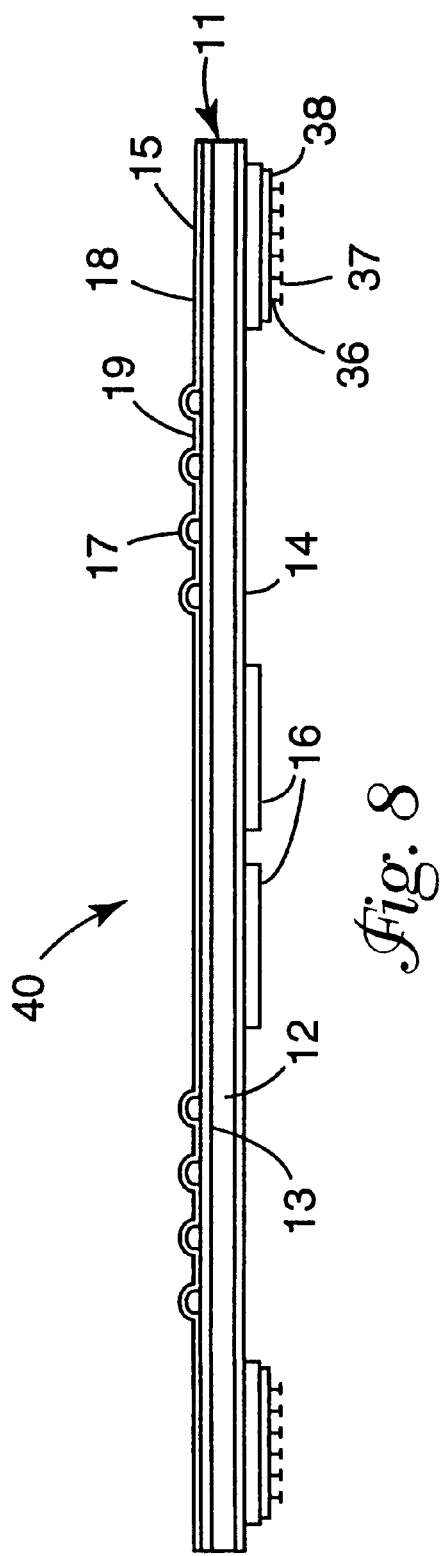
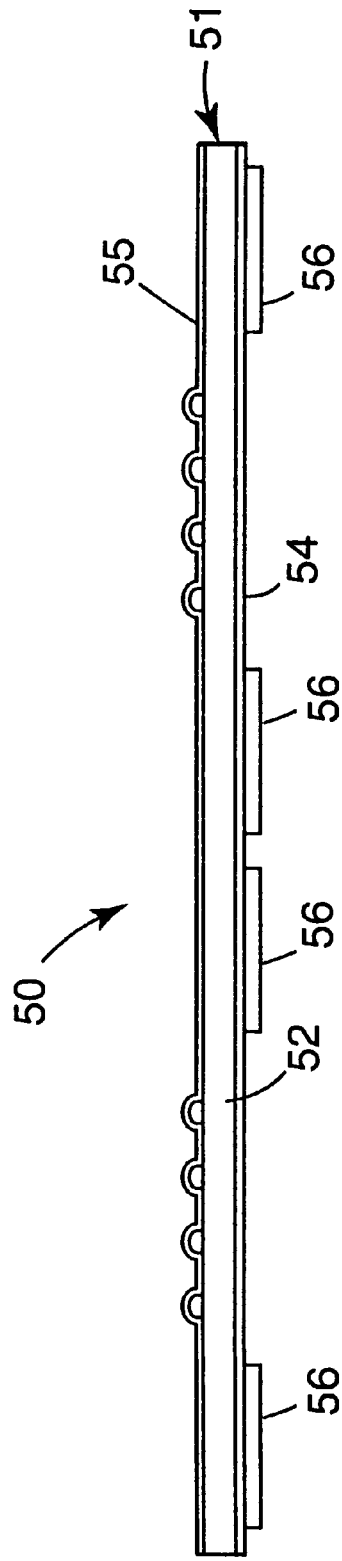

ELASTIC TAB LAMINATE

BACKGROUND AND FIELD OF THE INVENTION

The present invention relates to a extensible elastic tab useable as a fastening tab for closure of limited use garments and disposable absorbent articles such as diapers and incontinent briefs, training pants, diaper liners, sanitary hygiene articles and the like.

The provision of elastic on or adjacent the body engaging portions of limited use garments and disposable absorbent garments is widespread both in the patent art and in commercial products, where generally elastic films, strands, nonwovens or foam materials are used. These elastic materials when applied directly to a limited use garment or disposable absorbent article, in the area intended to engage a body portion of a wearer, are generally applied to the garment or article in an extended state. When the extended elastic recovers it gathers the material forming the body engaging portion, of the disposable absorbent article or limited use garment or the like, to which the elastic is attached. It has been proposed to provide only sections of the body-engaging portion with elastic. For example, in U.S. Pat. Nos. 4,857,067; 5,156,973 and 4,381,781, it has been proposed that elastic be provided only in an outwardly extending ear portion of a diaper. By placing the elastic in this outwardly extending ear portion, the engaging effect of the elastic is not deadened by reinforcement with the absorbent core. For example, when elastic in placed on a waistband portion (where elastic is typically located), the elastic can be reinforced by the absorbent core structure below the waistband. In U.S. Pat. No. 4,857,067 the elastic used is preferably a heat-shrinkable elastic which is applied in an extended unstable condition and allowed to recover by the application of heat. This causes the inelastic material of the ear portion attached to the elastic to gather. In U.S. Pat. No. 5,156,743 the elastic material is a conventional film-like elastic which is applied to a diaper in the ear portion in an untensioned state followed by a localized stretching of the resulting laminate in a location where the elastic is attached by meshing corrugating rolls which intermittently engage and disengage with the laminate material in a machine direction. The inelastic material of the ear is permanently deformed by this localized stretching and the deformed inelastic material gathers when the attached stretched elastic recovers. In U.S. Pat. No. 4,381,781 an elastic film is located in an ear portion of a diaper where non-elastic material in the ear portion has been cut out or removed so the elastic can be applied in an untensioned state and be relatively unhindered when extended.

It has also been proposed to provide elastic material outside the side edge of a disposable absorbent garment or the like in association with a fastening element. The fastening element when grasped, tensioned and secured causes the elastic to extend. The extended elastic then tensions the body-engaging portion to which it is operably attached. This approach is desirable in that the elastic need not be attached to the inelastic elements of the article in an extended state, which is difficult and the elastic is not reinforced by attached or adjacent inelastic material forming the article and its components. For example, providing a fastening tape or tab having a specific elastic region, is disclosed in U.S. Pat. No. 5,057,097 which proposes forming a fastening tab where the tab backing is a multi-layer film formed of an elastic center layer and inelastic outer layers. The coextruded material described must be stretched beyond a yield point or range after which the coextruded material exhibits elastic properties in a central region. Generally, the coextruded materials described were elongated to approximately 400%. Generally the force at 50% elongation for the second pull of the elastic material is a fraction of this 50% force of the inelastic material for the initial elongation. This is not desirable for a material that may be used on the first pull. Furthermore, the performance of this material is unpredictable in use. The end user has no clear indication of where they must stop pulling the elastic material in order to achieve activation (e.g., the initial force at 50% elongation is substantially the same as the initial force at 400% elongation). This initial elongation is important as the elastic performance in use, (i.e. on the second and subsequent pulls) is dictated by the extent to which the materials is initially stretched. The user may choose to extend the material 50% or 700% or somewhere in between. As such, the elastic performance in use is extremely variable depending on the particular user and how far he or she chooses to extend the tab initially.

Another elasticated fastening tape product is disclosed in European Patent 704196, which indicates that conventional elastic fastening tapes are provided by laminating the ends of stretchable and unstretchable portions, which provide unreliable connections in industrial conditions. This patent proposed that the entire stretchable elastic material be continuously attached to a center portion of a fastening tab which center portion is then subsequently selectively stretched by passing that portion of the laminate material through meshed corrugating rolls. This solution of course results in some of the same problems as attaching the elastic to the garment itself.

U.S. Pat. No. 5,549,592 describes a laminated fastening tape tab where the same problem of a weak bond between the ends of an elastic panel and a fastening tab is addressed by providing a reinforcement strip at this bonding location.

The provision of elastic panels on the outside of a disposable absorbent garment is also discussed in U.S. Pat. No. 5,669,897 (2 elastic panels are provided with different directions of extensibility attached at one end to a fastening tab and at the other end to the side edge of the disposable absorbent garment). U.K. Patent Application 2,284,742, which is similar to U.S. Pat. No. 5,549,592, provides a specific reinforcement material at the location near a fastening tab is joined to an elastic panel section. However, this reinforcement is provided at locations other than directly at the bond point between the fastening tab and the elastic panel providing a "stress beam section" to facilitate in the distribution of forces across the elastic panel. U.S. Pat. No. 5,399,219 also discloses an elastic panel fastening tab similar to that of 5,549,592, however providing a stiffening material which is attached to both the tape backing material and the side panels. In U.S. Pat. Nos. 5,593,401; 5,540,796 and U.K. Application 2,291,783 side panels are attached to bridging members which connect to laterally opposed side panels.

SUMMARY OF THE INVENTION

The invention relates to an extensible elastic tab designed to be adhered to the edge of an article, formed using a coextruded elastic film comprising at least one elastic layer and at least one second layer on at least a first face of the elastic layer. One face of the coextruded elastic film is attached to at least a partially extensible nonwoven layer. The partially expandable, or extensible nonwoven layer has at least one first portion with limited extensibility in a first direction and at least one second inextensible portion in the first direction. The extensible elastic tab when stretched to the extension limit of the first portion or portions in the first direction will elastically recover at least 1.0 cm, preferably at least 2 cm providing an elastic tab having a Useful Stretch Ratio (as defined in the Examples) of at least 30 percent. The Useful Stretch Ratio includes the portion of the elastic recovery length having an elastic recovery force of greater than 20 grams/cm force, but below a given extension which generally is 90 percent of the extension limit. Further the elastic tab in the region of the Useful Stretch Ratio preferably has an incremental extension force of less than about 300 grams/cm. The coextruded elastic film second layer is preferably a relatively inelastic material or blend and provided on both faces of the at least one elastic layer.

BRIEF DESCRIPTION OF THE DRAWINGS

FIG. 2 is a side view of an extensible elastic fastening tab composite material in accordance with the present invention.

FIG. 3 is a perspective view of an extensible elastic fastening tab formed from the FIG. 2 composite material.

FIG. 4 is a side view of an extensible elastic fastening tab composite material according to a second embodiment of the invention.

FIG. 5 is a perspective view of an extensible nonwoven usable in an elastic fastening tab according to a third embodiment of the invention.

FIG. 6 is a perspective view of the extensible nonwoven of FIG. 5 in an extended state.

FIG. 7 is a side view of an extensible elastic fastening tab material in accordance with the third embodiment of the present invention.

FIG. 8 is a side view of an extensible elastic fastening tab in accordance with a fourth embodiment of the present invention.

FIG. 9 is a side view of an extensible elastic fastening tab in accordance with a fifth embodiment of the present invention.

DETAILED DESCRIPTION OF THE PREFERRED EMBODIMENTS

Figure 1:
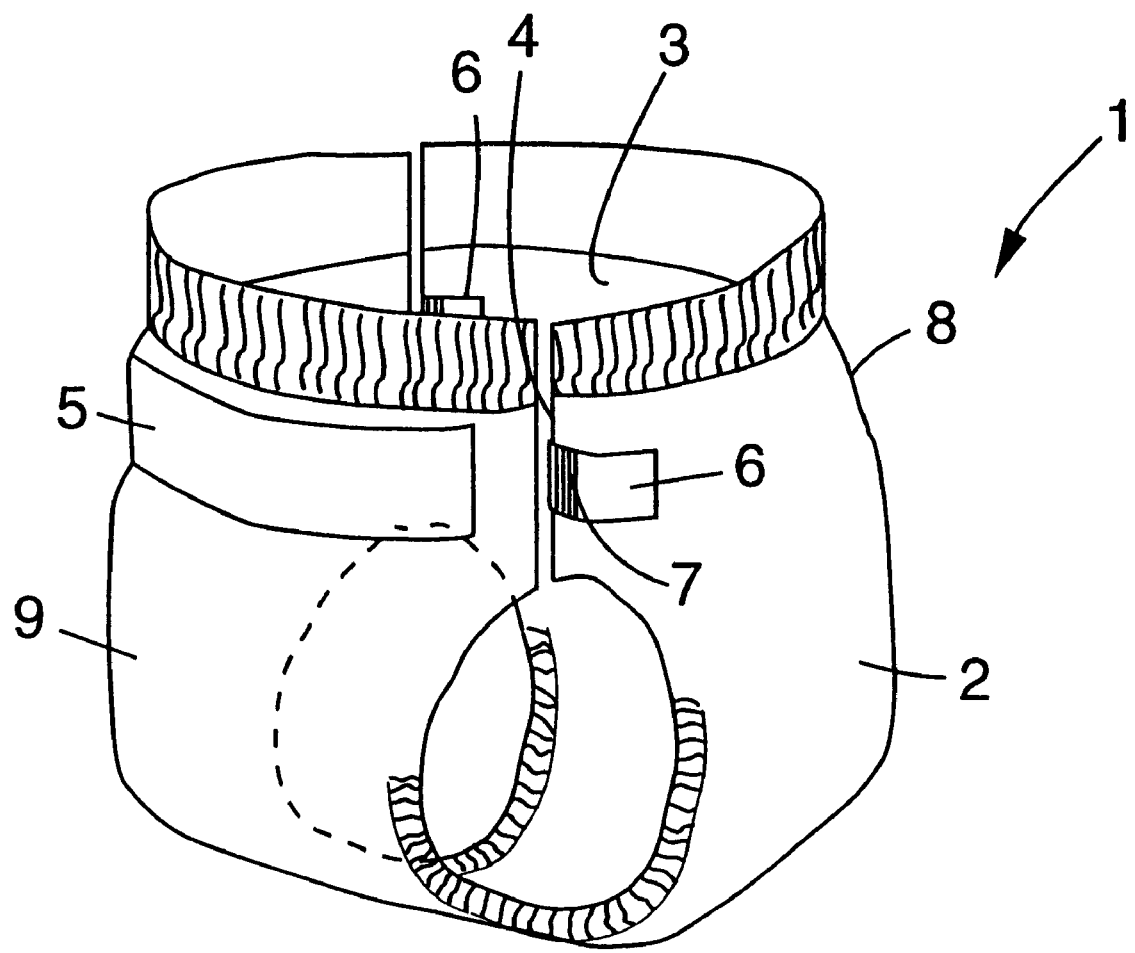
FIG. 1 is a perspective view of a disposable absorbent article using an extensible elastic fastening tab in accordance with the present invention.

The invention extensible elastic tab is formed using a coextruded elastic film comprising at least one elastic layer and at least one second layer of a relatively inelastic material on at least a first face of the elastic layer. The coextruded elastic film is attached to at least a partially extensible nonwoven layer on at least one face which allows the elastic film to stretch in the extensible portion of the nonwoven layer up to an expansion limit of this portion of the nonwoven layer. Beyond this expansion limit the incremental forces required to further stretch the extensible nonwoven layer portion increase generally by at least 100 grams/cm, preferably at least 200 grams/cm. This increase in force generally corresponds to the forces needed to start deforming the nonwoven layer and provides a clear signal to the user to stop pulling. In this manner the extensible elastic tab will have predictable elastic performance from one user to the next by virtue of this force increase signal causing users to uniformly extend the tab to substantially the same extension limit.

The extensible elastic tab when extended to the extension limit provided by the expandable or extensible portions of the nonwoven layer will elastically recover by the elastic forces provided by the coextruded elastic layer. For a given tab the length of this elastic recovery is preferably at least 1.0 cm, preferably at least 2.0 cm and most preferably 2.0 to 7.0 cm for use in most disposable or limited use garments. Elastic recovery in this range allows the elastic tab to be placed on a user in at least a partially extended state and accommodate for limited changes in dimension caused by, for example, breathing, muscular extensions, or the like, without being extended beyond the extension limit of the nonwoven layer or below the relaxed dimensions of the elastic layer. For other uses, this elastic recovery can be more or less depending on the range of expansion and adjustability that needs to be accommodated. Within this elastic recovery length there is generally a range where the elastic is useful. By useful it is meant that the elastic recovery forces and incremental extension forces are sufficiently large to engage a wearer but not so high as to cause bruising or red marking. The lower elastic recovery force limit is generally about 20 grams/cm force and the upper extension force limit is generally in the range of about 300 to 350 grams/cm. However, red marking depends on the individual and their susceptibility to bruising. Some individuals, mainly adults, can be subject to higher forces without red marking while some individuals may red mark at lower forces, generally fair skinned adults and/or children or infants. The useful range of the elastic tab is also limited by the extension limit of the attached nonwoven layer. Generally, the elastic tab in use will be used at an extension below this extension limit, generally at about 90 percent or less of the extension limit. The useful elastic range of the elastic tab of the invention can be expressed as a ratio of the useful range of elasticity (e.g. from 20 grams/cm force to 90 percent of the extension limit; provided that the incremental extension forces at this extension are below the red marking force limit for the intended use) divided by the total potential elastic range (e.g., 90 percent of the extension limit). Generally this Useful Stretch Ratio (USR) should be greater than 30 percent preferably greater than 40 percent.

This Useful Stretch Ratio is determined first by the coextruded elastic. For example, decreases in the potential useful stretch ratio can be due to the composition and thickness of the second skin layers, the degree of bonding of the coextruded elastic to the extensible portion of the extensible nonwoven layer portion and the degree if any to which the extensible nonwoven layer portion restricts extension of the coextruded elastic layer prior to the extension limit being reached. With thicker or more rigid skin layer materials the USR generally decreases, also the incremental extension forces increase substantially on the first, as well as on the subsequent extensions, making the elastic more likely to cause red marking. Thicker skins or more rigid skins also increase the degree of permanent set in the coextruded elastic. Thinner or softer skin layers allow the elastic tab to easily extend at low elongations and still have relatively high Useful Stretch Ratios as well as relatively constant elastic properties over the Useful Stretch Ratio (e.g. relatively low hysteresis loss and flatter stress strain properties).

The nonwoven layer can be attached to only a portion of the coextruded elastic film; however for aesthetics, ease of manufacturability and performance reasons the nonwoven layer is generally coextensive with the coextruded elastic film. The nonwoven layer extensible portion(s), generally extends by at least 30 percent of its original length, preferably at least 75 percent where the preferred range of extensibility is from 50 to 400 percent most preferably from 75 to 200 percent. These lower elongation or extension percentages make it easier for an end user to fully extend the tab to the extension limit of the extensible portions, which provides for more predictable and reproducible elastic performance for the tab.

Referring to FIG. 1, there is shown a perspective view of a conventional diaper which could employ the extensible elastic tab of the invention as a fastening tab on the diaper 1. The diaper 1 is of conventional type construction having a flexible backing 2, which would be liquid impermeable or substantially liquid impermeable and generally be formed of a film, or a laminate of a film and a nonwoven layer. The backing layer 2 could also be moisture and gas permeable and liquid impermeable. An absorbent core structure 9 is generally sandwiched between the backing 2 and a liquid permeable facing layer 3. The liquid permeable facing 3 is generally a nonwoven web but could also be a perforated film, or the like. The extensible elastic tab is provided as a fastening tab 6 adjacent side edges 4 on a top back portion 8 of the diaper 1. If necessary, a complementary fastening element 5 is provided which will engage with a fastening element provided on a distal end of the extensible elastic fastening tab 6.

The extensible elastic tab of the invention can be used with other disposable absorbent articles, limited use garments or the like as a fastening tab when provided with one or more fastening elements. The extensible elastic tab can also be used as a bandage material, an elastic connector or the like with associated fastening elements. When used without fastening elements the extensible elastic tab can also be used to elasticate caps, garments, booties, headbands, sport wraps or the like. In these uses one or both ends of the tab would be permanently attached to the article to be elasticated such as by heat bonding, ultrasonic bonding, sewing or the like.

A first embodiment of an extensible elastic tab of the invention as an extensible elastic fastening tab material 10 is shown in FIG. 2. FIG. 2 shows a side perspective view of an indefinite length of fastening tab material 10 laminate. Individual fastening tabs would be cut from this material, for example, by using a knife slitter, or the like, to slit the web of material 10 in the center resulting in two continuous webs of extensible fastening tab material. Individual fastening tabs 22 as shown in FIG. 3 can be cut from the single tab width web materials by a die cutter or the like with a preselected width dimension. Generally, the extensible elastic portion 7 of an individual tab would have a width 21 of from 1 to 10 cm, preferable 2 to 7 cm.

The individual tab 22 can be cut into a rectangular shape as shown in FIG. 3. Other shapes are also possible such as those disclosed in European Patent No. 233704 (Burkhard et al); Japanese Patent Kokai Sho 63-249704 (Yamamoto et.al.); European Patent No. 379,850 (Aronson et. al.) and U.S. Pat. Nos. 5,312,387 (Rossini et. al.) and DES 377,979 (Plaschko et. al.). In Rossini et. al. the fastening tabs are provided with a free end distal half (maximum width x-y), a proximal half (minimum width y) and a manufacturers end (width x). The extensible free end portion of the invention elastic tab would preferably be provided in the proximal half region of the fastening tab free end shape of Rossini et al. The Rossini et al. shape can nest with opposite facing free ends such that tabs can be cut from a standard roll of material with little or no waste. This shape tapers outward on the free end. Shapes that taper inward on a fastening tab free end are described in Plaschko et al. and Aronson et al; however, these described shapes do not nest so that salvage material must be discarded. In Yamamoto et. al. and Burkhard et. al. similar shapes are shown where the free ends taper more dramatically so that the opposing free ends can nest with each other allowing tabs to be cut from opposite sides of the roll of tape with the free ends nested in an alternating array allowing for no waste or salvage. These designs are less desirable as the elastic regions would be generally wider than the region (the free end proximal half) provided with the fastening elements (the free end distal half). A thinner elastic would sometimes be needed so that this wider elastic would not cause the smaller fastening elements to detach or cause red marking on the wearer. Thinner elastics, however, would result in less robust tabs that could curl and be more difficult to grasp and apply as a fastening tab.

The extensible elastic tab is provided with one or more relatively inextensible zones or portion 18 and one or more relatively extensible zones or portions 7. The extensible zones 7 are elastic due to the attached coextruded elastic film material 11. By inextensible it is meant that zones 18 will not extend under average tensions imposed by an average consumer. Generally, the zones 18 will not extend significantly when placed under a force of about 300 grams/cm or less, preferably 400 grams/cm or less. This inextensibility is provided primarily by the nonwoven web layer 15 which in inextensible zones 18 has at least a portion thereof coplanar with the underlying elastic layer in the direction in which the tab is intended to be extended. In FIG. 2 the direction of intended extensibility is shown by arrows and the nonwoven web layer 15 is coplanar with the coextruded elastic layer 11 in both the extensibility direction and the cross direction (i.e., into the paper). Although not shown in FIG. 2 the nonwoven web layer could be coplanar with the elastic layer in one or more cross directions, or even partially coplanar with the elastic layer 11 in the extensibility direction, as long as the nonwoven web layer reinforces the inextensible zones 18 to prevent extension of these zones under forces such as described above.

The extensible zones 7 are provided by rendering the substantially inelastic nonwoven layer 15 extensible in the extensible zones 7 in the direction, or directions, of intended extensibility. In the FIG. 2 embodiment this extensibility is provided in zones 7 by making the nonwoven web layer 15 noncoplanar with the underlying elastic layer 11 in the direction of extensibility. By noncoplanar it is meant that the nonwoven web layer 15 length (in the plane of the web 15) in the direction of intended extensibility is greater than the length (in the plane of the film layer 11) of the underlying elastic film layer 11 such that the underlying elastic film layer 11 can be extended without permanent deformation of the bulk of the nonwoven web layer 15. As such, the nonwoven web layer 15 is nonplanar with the underlying elastic layer 11 along the entire, or substantially all of the, width (the orthogonal cross direction to the extensibility direction) of the extensible elastic tab undergoing extension in the extensible zones 7.

The nonwoven layer 15 in the FIG. 2 embodiment is intermittently attached to the elastic film layer 11 at linear attachment regions 19 with arcuate portions 17 projecting outward from adjacent linear attachment regions 19. The length of the nonwoven web layer 15 in the arcuate portions 17 is greater than the length of the elastic film material 11 between the same two adjacent attachment regions 19. In the FIG. 2 embodiment the attachment regions 19 are mutually parallel, substantially linear, equally spaced and orthogonal to the direction of extensibility. This is a preferred arrangement for uniform elastic properties; however, the attachment regions 19 could be nonlinear or intermittent (e.g. point bond, segmented bond lines, circular bonds or the like) and/or randomly spaced and substantially parallel and still provide uniform elastic properties. Uniform elastic properties are also possible with point bonds or bond regions arranged in a uniform array or geometric pattern or with nonlinear bond lines that intersect in a uniform geometric pattern.

By uniform geometric pattern it is meant that the amount of nonwoven material between, or within, a given bond pattern is substantially uniform across the length and width of the extensible portion 7. Nonuniform elastic properties could be provided by providing attachment regions that are nonparallel. For example, the attachment region spacing could vary in the cross direction of the extensible elastic tab providing a tab with differing degrees of elasticity along its width. For example bond points or lines could be randomly spaced, converge, diverge, or increase in size and/or frequency. Also elastic properties can be varied by changing the amplitude or size of one or more of the arcuate portions either in the direction of extensibility or the width direction. Generally, the ratio of the length of an arcuate portion to the underlying elastic between attachment regions is substantially constant at in any given point along the first direction. If this ratio is significantly smaller for a given arcuate portion this particular arcuate portion would reach its extension limit, without deformation, prior to other adjacent arcuate portions in the first direction. Further stretch would then occur in the remaining arcuate portions until their extension limit(s) were reached. However any further incremental extension forces would tend to concentrate in this section of the nonwoven web that reached its extension limit first making the elastic tab as a whole less resistant to permanent deformation (at least in this section or sections) when extended in the first direction.

In general, the nonwoven web layer 15 is a bonded nonwoven web having a tensile initial yield force of at least 100 gram/cm, preferable at least 300 grams/cm. Suitable processes for making the nonwoven web include, but are not limited to, airlaying, spunbond, spunlace, bonded melt blown webs and bonded carded web formation processes. Spunbond nonwoven webs are made by extruding a molten thermoplastic as filaments from a series of fine die orifices in a spinneret. The diameter of the extruded filaments is rapidly reduced under tension by, for example, by noneductive or eductive fluid-drawing or other known spunbond mechanisms, such as descried in U.S. Pat. No. 4,340,563 (Appel, et al.); U.S. Pat. No. 3,692,618 (Dorschner et al.); U.S. Pat. Nos. 3,338,992 and 3,341,394 (Kinney); U.S. Pat. No. 3,276,944 (Levy); U.S. Pat. No. 3,502,538 (Peterson); U.S. Pat. No. 3,502,763 (Hartman); and U.S. Pat. No. 3,542,615 (Dobo et al.) The spunbond web is preferably bonded. The nonwoven web layer also may be made from bonded carded webs. Carded webs are made from separated staple fibers, which fibers are sent through a combing or carding unit which separates and aligns the staple fibers in the machine direction so as to form a generally machine direction-oriented fibrous nonwoven web. However, randomizers can be used to reduce this machine direction orientation. Once the carded web has been formed, it is then bonded by one or more of several bonding methods to give it suitable tensile properties. One bonding method is powder bonding wherein a powdered adhesive is distributed through the web and then activated, usually by heating the web and adhesive with hot air. Another bonding method is pattern bonding wherein heated calender rolls or ultrasonic bonding equipment are used to bond the fibers together, usually in a localized bond pattern though the web can be bonded across its entire surface if so desired. Generally, the more the fibers of a web are bonded together, the greater the nonwoven web tensile properties.

Airlaying is another process by which fibrous nonwoven webs useful in the present invention can be made. In the airlaying process, bundles of small fibers usually having lengths ranging between about 6 to about 19 millimeters are separated and entrained in an air supply and then deposited onto a forming screen, often with the assistance of a vacuum supply. The randomly deposited fibers are then bonded to one another using, for example, hot air or a spray adhesive.

Alternatively known melt blown webs or spunlace nonwoven webs or the like can be used to form the nonwoven webs of the invention extensible elastic tabs. Melt blown webs are formed by extrusion of thermoplastic polymers from multiple die orifices, which polymer melt streams are immediately attenuated by hot high velocity air or steam along two faces of the die immediately at the location where the polymer exits from the die orifices. The resulting fibers are entangled into a coherent web in the resulting turbulent airstream prior to collection on a collecting surface. Generally, to provide sufficient integrity and strength for the present invention, melt blown webs must be further bonded such as by through air bonding, heat or ultrasonic bonding as described above.

The elastic film layer 11 is a coextruded elastic film, such as disclosed in U.S. Pat. Nos. 5,501,675; 5,462,708; 5,354,597 or 5,344,691, the substance of which are substantially incorporated herein by reference. These references teach various forms of multilayer coextruded elastic laminates, with at least one elastic core layer and either one or two relatively inelastic skin layers. The skin layers (13 and 14) can be stretched beyond an elastic limit of these skin layers (i.e., they are permanently deformed) and the coextruded laminate subsequently recovered in the direction opposite to the stretching direction by the relatively higher elastic recovery forces of the elastic core layer.

The skin layers (13 and 14) recover little or at least less than the elastic core layer 12 and can form a microtextured or microstructured surface on the elastic core layer 12. This is similar to gathering but on a much smaller scale and more regular. Microtexture or microstructure means that the skin layer (13 or 14) contains peak and valley irregularities or folds which are large enough to be perceived by the unaided human eye as causing increased opacity over the opacity of a laminate before stretching and recovery. The irregularities are small enough to be perceived as smooth or soft on human skin and magnification is required to see the details of the microtexturing.

The skin layers (13 and 14) are generally nontacky materials or blends formed of any semicrystalline or amorphous polymer(s) which are less elastomeric than the elastic core layer, generally inelastic, and which will undergo relatively more permanent deformation than the core layer 12 at the percentage that the elastic laminate 11 is stretched. Elastomeric materials such as olefinic elastomers, e.g., ethylene-propylene elastomers, ethylene propylene diene polymer elastomers, metallocene polyolefin elastomers or ethylene vinyl acetate elastomers, or styrene/isoprene, butadiene or ethylene-butylene/styrene (SIS,SBS or SEBS) block copolymers, or polyurethanes or blends with these materials can be used as long as the skin layers provided are generally nontacky and preferably can act as barrier layers to any adhesive applied. Generally, the elastomeric materials used are present in a blend with nonelastomeric materials in a weight percent range of 0–70%, preferably 5–50%. High percentages of elastomer in the skin layer(s) generally require use of antiblock and/or slip agents to reduce the surface tack and roll unwind force. Preferably, these skin layers are polyolefinic formed predominately of polymers such as polyethylene, polypropylene, polybutylene, polyethylene-polypropylene copolymer, however, these skin layers may also be wholly or partly polyamide, such as nylon, polyester, such as polyethylene terephthalate, or the like, and suitable blends thereof. Generally, the skin layer material following the stretching and recovery of the coextruded elastic is in contact with the elastic core layer material in at least one of three suitable modes; first, continuous contact between the elastic core layer and the microtextured skin layer; second, continuous contact between the layers with cohesive failure of the core layer material under the microtextured skin folds; and third, adhesive failure of the skin layer to the core layer under the microtextured folds with intermittent skin layer to core layer contact at the microtexture fold valleys. Generally, in the context of the present invention, all three forms of skin-to-core contact are acceptable. However, preferably the skin and core layers are in substantially continuous contact so as to minimize the possibility of delamination of the skin layer(s) from the elastic core layer.

Generally, the overall core layer 12 to skin layer(13 and 14 combined) thickness ratio of the coextruded film will be at least 1.5, preferably at least 5.0 but less than 1000 and most preferably from 5.0 to 200. Generally, the overall caliper of the multilayer film is preferably 25 to 200 microns. The addition of the skin layer materials generally tends to reinforce the elastic film material as described in the above patent documents. However, in the present invention the skin layers are provided to be sufficiently thin and/or soft so that little or no reinforcement of the elastomeric core layer occurs and the coextruded film is elastic in its initial elongation as well as its second and subsequent elongations at suitably low stress elongation forces and low hysteresis loss levels when the elastic is cycled in use (e.g. by dimensional changes caused by breathing). Generally, the coextruded elastic film has elastic properties on its first and preferably its subsequent elongations similar to that of the elastomeric layer material itself with no distinct yield point or range in the first elongation.

The elastomeric core layer 12 is formed of a material, which exhibits elastomeric properties at ambient conditions. Elastomeric means that the material will substantially resume its original shape after being stretched. Preferably, the elastomer will sustain only small permanent set following deformation and relaxation, which set is preferably less than 30 percent and more preferably less than 20 percent of the original 50 to 500% stretch. The elastomeric material can be either pure elastomers or blends with an elastomeric phase or content that will still exhibit substantial elastomeric properties at room temperature. Suitable elastomeric thermoplastic polymers include block copolymers such as those known to those skilled in the art as A-B or A-B-A type block copolymers or the like. These block copolymers are described, for example, in U.S. Pat. Nos. 3,265,765; 3,562,356; 3,700,633; 4,116,917 and 4,156,673, the substance of which are incorporated herein by reference. Styrene/isoprene, butadiene or ethylene-butylene/styrene (SIS,SBS or SEBS) block copolymers are particularly useful. (Generally, there are two or more blocks, at least one A-block and at least one B-block, where the blocks can be arranged in any order including linear, radial, branched, or star block copolymers). Other useful elastomeric compositions can include elastomeric polyurethanes, ethylene copolymers such as ethylene vinyl acetates, ethylene/propylene copolymer elastomers or ethylene/propylene/diene terpolymer elastomers. Blends of these elastomers with each other or with modifying non-elastomers are also contemplated.

Viscosity reducing polymers and plasticizers can also be blended with the elastomers such as low molecular weight polyethylene and polypropylene polymers and copolymers, or tackifying resins such as Wingtack™, aliphatic hydrocarbon tackifiers available from Goodyear Chemical Company. Tackifiers can also be used to increase the adhesiveness of an elastomeric layer to a skin layer. Examples of tackifiers include aliphatic or aromatic hydrocarbon liquid tackifiers, polyterpene resin tackifiers, and hydrogenated tackifying resins. Aliphatic hydrocarbon resins are preferred.

Additives such as dyes, pigments, antioxidants, antistatic agents, bonding aids, antiblocking agents, slip agents, heat stabilizers, photostabilizers, foaming agents, glass bubbles, reinforcing fiber, starch and metal salts for degradability or microfibers can also be used in the elastomeric core layer(s).

Figure 10:
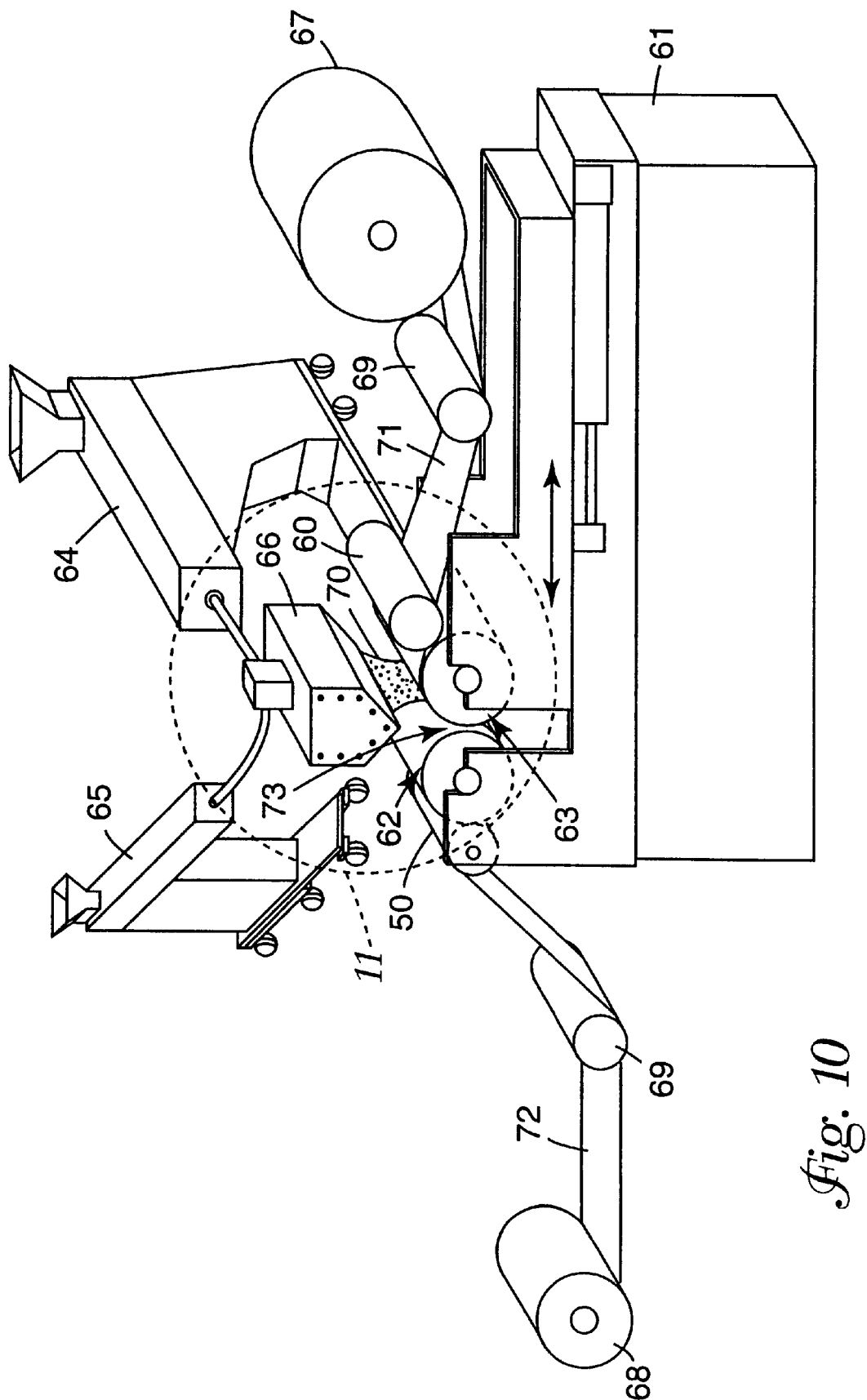
FIG. 10 is a perspective view of a method and apparatus for making the first embodiment of the extensible elastic fastening tab composite material of FIG. 2 of the present invention.
Figure 11:
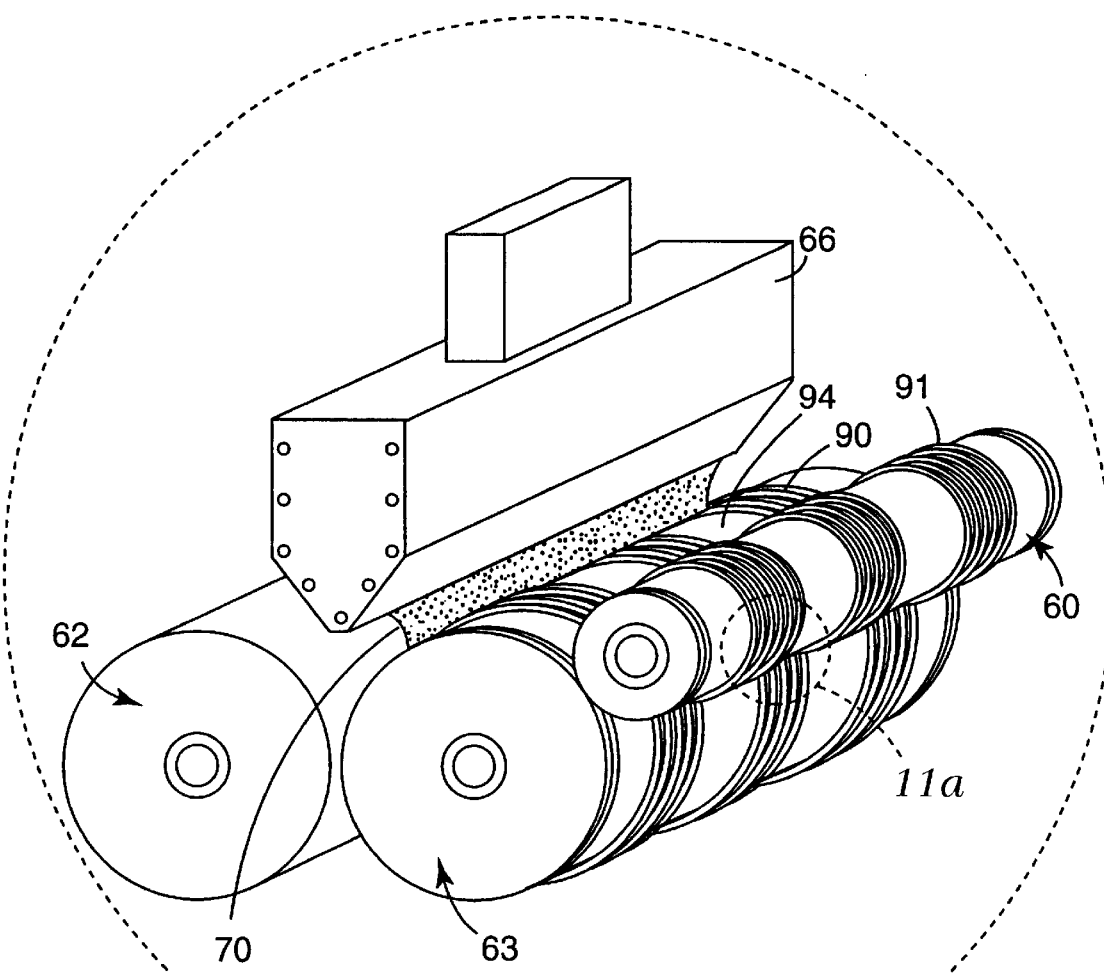
FIG. 11 is an enlarged sectional view of a portion of FIG. 10.
Figure 11A:
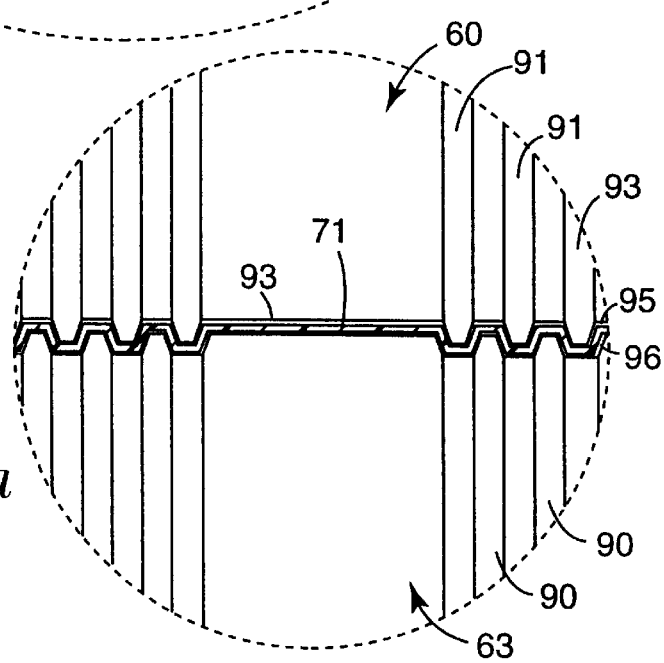

The invention laminate of FIG. 2 is provided by bonding the nonwoven web 15 to the coextruded elastic film 11. This can be done by heat bonding, extrusion bonding (as shown in FIGS. 10 and 11), adhesive bonding or the like. A suitable method for forming the invention laminate comprises (1) providing a first sheet of nonwoven natural and/or polymeric fibers that are internally bonded; (2) forming extensible portions of the first sheet of nonwoven material to have arcuate portions projecting in the same direction from spaced attachment regions of the first sheet of nonwoven material; (3) coextruding molten thermoplastic materials that form a resiliently elastic film when cooled (e.g., elastomeric core layers of polyester, polyurethane, polystyrene-polyisoprene-polystyrene, polystyrene-polybutadiene-polystrene or polystyrene-poly(ethylene-butylene)-polystyrene) onto the attachment regions and inextensible portions of the first sheet of nonwoven material to form, when cooled and solidified, a coextruded elastic film thermally bonded to and extending between the attachment region of the first sheet of nonwoven material and thermally bonded to the inextensible portions of the nonwoven layer.

In the method described above, the forming step (2) can comprise the steps of (a) providing first and second generally cylindrical corrugating members each having an axis and including a multiplicity of spaced ridges defining the periphery of the corrugating member, the ridges having outer surfaces and defining spaces between the ridges adapted to receive portions of the ridges of the other corrugating member in meshing relationship with the sheet of flexible material therebetween; (b) mounting the corrugating members in axially parallel relationship with portions of the ridges in meshing relationship; (c) rotating at least one of the corrugating members; and (d) feeding the sheet of nonwoven material between the meshed portions of the ridges conforming the sheet of flexible material to the periphery of the first corrugating member and forming the arcuate portions and the anchor portions of the sheet of nonwoven material along the ridges of the first corrugating member; and (e) retaining the nonwoven material on the first corrugating member for a predetermined distance after movement past the meshing portions of the ridges. The extruding step includes providing extruders that, through a die, coextrude the molten thermoplastic materials onto the attachment regions and the inextensible portions of the nonwoven material along the periphery of the first corrugating member within the predetermined distance.

The extensible elastic tab according to the present invention can further include a second sheet of nonwoven or other flexible material having attachment regions thermally bonded at second bonding locations of the coextruded elastic film second face.

A second embodiment of the invention extensible elastic tab material 20 intended to be used as a fastening tab is shown in FIG. 4. In all respects identical numbers indicate identical features discussed relative to the FIG. 2 embodiment. In the embodiment of FIG. 4 the extensible portion 7 of the nonwoven web layer 15 is provided by compacting the nonwoven web in the extensible portion 7, compacting can be accomplished, for example, by using the "Micrex/Microcreper" equipment available from Micrex Corporation, Walpole, Mass., that bears U.S. Pat. Nos. 4,894,169; 5,060,349; and 4,090,385. The nonwoven web 15 is compressed so that the sheet is compacted in a first direction along its surfaces and can be easily expanded in that first direction by partial straightening of the fibers in the nonwoven web.

FIGS. 5–7 show a third embodiment of the invention extensible elastic tab as a fastening tab. In this embodiment again identical numbers indicate identical features discussed relative to the FIG. 2 embodiment. In the embodiment of FIGS. 5–7 the extensible portion 7 is provided by skip slitting of the nonwoven web 15 in the extensible portion 7 as is disclosed in PCT WO 96/10481. The slits 37 can be discontinuous as shown in FIG. 5 and are generally cut on the nonwoven web 15 prior to the web being attached to the coextruded elastic film 11. Although more difficult, it is also possible to create slits in the nonwoven web layer after the nonwoven web 15 is laminated to the coextruded elastic film, in which case it is possible to form slits that extend across the entire width of the nonwoven web.

At least a portion of the slits 37 in the nonwoven layer 15 should be generally perpendicular (or have a substantial perpendicular vector) to the intended direction of extensibility or elasticity (the at least first direction) of the coextruded elastic layer 11. By generally perpendicular it is meant that the angle between the longitudinal axis of the chosen slit or slits and the direction of extensibility is between 60 and 120 degrees. A sufficient number of the described slits are generally perpendicular such that the overall laminate is elastic in the extensible portion 7. The provision of slits in two directions is advantageous when the elastic laminate 30 is intended to be elastic in at least two different directions.

FIG. 6 shows the extensible nonwoven web of FIG. 5 after it has been stretched, allowing the slits to open and expand in the direction of extension.

FIG. 7 shows a fastening tab 30 using the extensible nonwoven web 15 of FIG. 5. The nonwoven is bonded to the coextruded elastic film 11 in bonding or attachment regions 39.

In all the above discussed embodiments the extensible elastic tab of the invention has been illustrated as a fastening tab material provided with fastening elements 16, which in these embodiments is shown as an adhesive patch, generally a pressure-sensitive adhesive patch. These adhesive patches can be applied as discrete strip-coated areas directly onto the coextruded elastic film backing without concerns for migration of conventional tackifiers from the adhesive layer into the elastic film layer 12 due to the skin layer 14 being selected to act as a barrier layer. The adhesive layer can be any conventional solution or hot-melt coated adhesive such as a tackified synthetic rubber resin adhesive, an acrylate adhesive, a silicone adhesive, a polyalpha-olefin adhesive, blends or the like. The adhesive layer 16 can also be applied as a transfer adhesive or double-coated adhesive with a backing.

In FIG. 8 one of the adhesive fastening elements has been replaced with a mechanical fastening element 37, particularly a hook mechanical fastening element 37 having upstanding hook elements 36 and a backing layer 38. This mechanical fastening element 37 can be attached to the coextruded elastic film by use of hot melt or pressure-sensitive adhesives, heat bonding, ultrasonic bonding, or the like. Alternatively, loop mechanical fastening elements, interlocking mechanical fastening elements, or the like can be used. Preferably the mechanical fastening element 37 will have a backing layer or film 38 which is a thermoplastic material for ease of attachment and recyclability.

In the embodiment of FIG. 9, the elastic fastening tab material 50, coextruded elastic film laminate layer 51 has only one skin layer 54 and one elastic layer 52 joined to the nonwoven layer 55. The one elastic layer 52 is joined to the nonwoven layer 55 and the skin layer 54 is on the opposite face of the elastic layer 52 between the elastic layer and the attachment element adhesive 56.

If only one skin layer 54 is provided the skin layer 54 is preferable placed between the fastening elements provided and the elastic film layer 52. The skin layer material can provide a barrier layer to migration of tackifiers and other low molecular weight species into the elastic layer and also creates a more stable surface for attachment of the fastening elements, particularly when the skin layer is an inelastic material. The skin layer also is less tacky than the elastic layer material so is not as likely to bind to a users skin.

An apparatus for forming the invention extensible elastic laminate as shown in FIG. 2 is depicted in FIGS. 10 and 11. The equipment for performing the method includes first and second generally cylindrical corrugating members 63 and 60, each having an axis and including a multiplicity of spaced ridges (90, 91) defining the periphery of the corrugating member 63 or 60. The ridges (90, 91) have outer surfaces that define spaces, 93 and 96, between the ridges (90, 91). The ridges 91 of one corrugating member are adapted to receive portions of the ridges 90 of the other corrugating member in meshing relationship with the nonwoven material 71 therebetween. Means, for mounting the corrugating members 63 and 60 in axially parallel relationship is provided. Also provided, are means for rotating at least one of the corrugating members 63 or 60. When the sheet 71 of nonwoven material is fed between the meshed portions of the ridges 90 and 91, the sheet 71 of nonwoven material will generally conform to the periphery 96 of the first corrugating member 63 to form arcuate portions of the nonwoven material 71 in the spaces between the ridges 90 of the first corrugating member 63. Attachment regions are formed along the outer surfaces of the ridges 90 of the first corrugating member 63. The surface 96 of the first corrugating member 63 is generally roughened by being sand blasted or chemically etched and heated to a temperature generally in the range of 10 to 150 Celsius above the temperature of the first sheet 71 nonwoven material. This helps retain the nonwoven material 71 along the periphery of the first corrugating member 63 for a predetermined distance after movement past the meshing portions of the ridges 90 and 91. A die 66 is fed the elastic thermoplastic material (e.g., elastomeric polyester, polyurethane, polystyrene-polyisoprene-polystyrene, polystyrene-polybutadiene-polystyrene or polystyrene-poly(ethylene-butylene)-polystyrene, or the elastomeric polyolefin described in European Patent Application No. 416815, or the elastomeric low density polyethylene, such as sold by Dupont Dow elastomers under the trade name "Engage") by a first extruder 64, and at least one layer of a relatively inelastic skin layer material by a second extruder(s) 65 to form the coextruded elastic film 70. The molten coextruded film 70 is positioned on the attachment regions 19 of the first sheet 71 of nonwoven material along the periphery of the first corrugating member 63 within the predetermined distance. The equipment further includes a generally cylindrical cooling roll 62 having an axis. The cooling roll 62 is rotatably mounted in axially parallel relationship with the corrugating members 63 and 60. The periphery of the cooling roll 62 is closely spaced from and defines a nip 73 with the periphery of the first corrugating member 63 at a predetermined distance from the meshing portions of the ridges 90. A nipping roller 50, or the like moves the extensible elastic tab composite 71 for a predetermined distance around the periphery of the cooling roll 62 past the nip 73 with the elastic film 70. This contact with the cooling roll cools and solidifies the elastic film 70.

TEST METHODS

Useful Stretch Ratio

The Useful Stretch Ratio is used to help define the elastic properties of the invention. A 2.54 cm×10.2 cm piece of film, cut in the cross-direction, was mounted in a tensile testing machine (Instron™ Model 55R1122 available from the Instron Corp.) with the upper and lower jaws 2.54 cm apart. Line-contact jaws were used to minimize slip and breakage in the jaws. The jaws are then separated at a rate of 12.7 cm/min (first upload) for 2.54 cm (100% elongation), 5.08 cm (200% elongation) or 10.16 cm (400% elongation). The jaws are then held stationary for 1 second after which they return (first download) to the zero elongation position. The jaws are again held stationary for 1 second after which they are returned (second upload) to the 100%, 200% or 400% elongation position at a rate of 12.7 cm/min. The jaws are again held stationary for 1 second after which they are returned (second download) to the zero elongation position to conclude the test. The Useful Stretch Ratio is calculated by subtracting the elongation at which the elastic recovery force equals 20 grams/cm during the first download from 90% of the total initial elongation, dividing by 90% of the total initial elongation, and expressing the result as a percent.

$F_{90}$;$2^{nd}$ Upload

The potential of putting red-marks on a baby's skin is determined by the $F_{90}$ on the second upload curve from the above-mentioned test. It is defined as the incremental extension force in grams/cm at the point that the second upload curve reaches 90% of the initial elongation (based on the $1^{st}$ upload curve) and is reported in the following tables as grams/centimeter of sample width.

Film & Layer Thickness

The individual layers of the films of this invention are typically very thin (usually <30 microns), and thus it can be difficult to measure their thicknesses by conventional photo-microscopy techniques. The thicknesses of the films in the following tables, except film samples 17–20, were determined via weight and density calculations. A 2.54 cm×15.24 cm strip of film was weighed to 4 decimal points on a Sartorius Analytic scale Model #A120S (Brinkman Instruments, Inc. Westbury, N.Y.) and then dissolved in toluene for 24 hours. The block copolymer elastomeric component and polystyrene component are soluble in toluene, whereas, the polyolefin components are not soluble. The toluene solution was filtered through a Buchner™ funnel to collect the insoluble fraction on filter paper. The filter paper was dried for 1 hour at 70° C., allowed to equilibrate to room temperature for 1 hour, and then weighed to 4 decimal points on the above mentioned Sartorius Analytic scale. By using the weight (before and after dissolving), the area, and the density, layer thicknesses were calculated. The layer thicknesses of film samples 17–20 were determined by fracturing the films under liquid nitrogen, taking a photograph with an optical microscope, and measuring the layers in the photograph with length measurement software.

Core:Thickness Ratio

The thickness of the elastic core layer for each sample is divided by the total thickness of the two sldn layers added together to arrive at the Core:Skin Thickness Ratio.

Stress Decay$_{250}$;$1^{st}$ Upload

The ability of the coextruded elastic films, used in the elastic tabs of this invention to retain a given force after stretching (first upload) over time is determined by the Stress Decay$_{250}$;$1^{st}$ Upload test. A 2.54 cm×10.2 cm piece of film, cut in the cross-direction, was mounted in a tensile testing machine (Instron™ Model 55R1122 available from the Instron Corp.) with the upper and lower jaws 5.08 cm apart. Line-contact jaws were used to minimize slip and breakage in the jaws. The jaws are then separated at a rate of 50.8 cm/min for 12.7 cm (250% elongation). The jaws are then held stationary for 1 minute after which they return to the zero elongation position. Elastic recovery force is measured at the point that the sample initially reaches 250% elongation and at the end of the 1-minute holding period. The difference between the initial force and the ending force is expressed as a percentage of the initial force and is referred to as Stress Decay$_{250}$;$1^{st}$ Upload.

Stress Decay$_{70}$;$2^{nd}$ Upload

The ability of the coextruded elastic films, used in the elastic tabs of this invention to retain a given force after stretching (second upload) over time is also determined by the Decay$_{70}$;$2^{nd}$ Upload test. A 2.54 cm×10.2 cm piece of film, cut in the cross-direction, was mounted in a tensile testing machine (Instron™ Model 55R1122 available from the Instron Corp.) with the upper and lower jaws 5.08 cm apart. Line-contact jaws were used to minimize slip and breakage in the jaws. The jaws are then separated at a rate of 50.8 cm/min for 2.54 cm (100% elongation), held stationary for 1 second and then returned to the 60% elongation (1.52 cm) position. The jaws are held for 20 seconds and then separated at a rate of 50.8 cm/min for 0.25 cm (70% elongation based on the original 2.54 cm sample length). The jaws are then held stationary for 1 minute after which they return to the zero elongation position. Elastic recovery force is measured at the point that the sample initially reaches 70% elongation on the 2nd upload curve and at the end of the 1-minute holding period. The difference between the initial force and the ending force is expressed as a percentage of the initial force and is referred to as Stress Decay$_{70}$;$2^{nd}$ Upload.

Unwind Force

The films of this invention are typically produced in large rolls. It is well known that elastic films can exhibit blocking. Blocking is the tendency of a layer of film to adhere to an adjacent layer of film leading to difficulties in unwinding the roll. Unwind Force is used to measure the ease at which rolls of film of this invention can be unwound. A roll of film 15.24 cm wide containing approximately 100–200 meters of film was placed on a free turning spindle which was attached on one end to a metal rod which was mounted in the lower jaws of an Instron™ Model 4501 tensile testing machine. The outside end of the film on the roll is clamped to the upper jaws. The jaws are then separated at a rate of 50.8 cm/min until approximately 15.24 cm of film have been unwound off the roll. The force vs. displacement plot will typically show an initial region of rapidly increasing force followed by a region of relatively constant force. The average force in the relatively constant region is divided by the width of the film roll and is expressed as the Unwind Force in grams/cm.

COEXTRUDED ELASTIC FILM SAMPLES

Film Samples 1–20

Three layer films were prepared on a coextrusion cast film line using 3 extruders to feed a Cloeren™ (Cloeren Co., Orange, Tex.) ABBBC feedblock. The A layers (first sldn layer) of film samples 1–20 were extruded with a 6.35 cm diameter single screw extruder (24:1 L/D) manufactured by Sterling Extruder (B&P Process Equipment and Systems Sagina, Mich.). Fina 3825 polypropylene was used for the A layers of film samples 1–7 and was extruded at a melt temperature of 208° C. The B layers (the elastomeric core) of film samples 1–20 were extruded with a 6.35 cm diameter single screw extruder (32:1 LED) manufactured by U.S. Extrusion Incorporated (Hawthorne, N.J.). Shell Kraton G1657 SEBS rubber was used for the B layers of film samples 1–16 and was extruded at a melt temperature of 214° C. The C layers (second skin layer) of film samples 1–20 were extruded with a 3.81 cm diameter single screw extruder (24:1 L/D) manufactured by Hartig (Battenfeld Blowmolding Machines, Boonton, N.J.). Fina 3825 polypropylene was used for the C layers of film samples 1–7 and was extruded at an average melt temperature of 198° C. DuPont Elvax™ 3174 EVA was used for the A layers of film samples 8–12 and was extruded at a melt temperature of 197° C. DuPont Elvax™ 3174 EVA was used for the C layers of film samples 8–12 and was extruded at a melt temperature of 190° C. Huntsman 1058 low density polyethylene was used for the A layers of film samples 13–16 and was extruded at a melt temperature of 207° C. Huntsman 1058 low density polyethylene was used for the C layers of film samples 13–16 and was extruded at a melt temperature of 200° C. DuPont Elvax™ 3174 EVA was used for the A layers of film samples 17–20 and was extruded at a melt temperature of 207° C. The B layer of film samples 17–20 was a blend of Dexco Vector™ 4111 SIS rubber (68%), Huntsman, 11S12A polypropylene (30%), and Techmer 1642E4 LDPE/TiO$_2$(50:50) white concentrate (2%) and was extruded at a melt temperature of 214° C. Fina 3825 polypropylene was used for the C layers of film samples 17–20 and was extruded at an average melt temperature of 200° C. The 3 layer films were extruded into a nip formed with a rubber roll and patterned steel roll with the C layer being in contact with the steel roll. Linespeed and extruder RPM's were varied in film samples 1–7, 8–12, 13–16, and 17–20 to produce four series of films with increasing core-:skin thickness ratio but with relatively constant core and total film thickness.

Film Samples 21–32

Three layer films were prepared on a coextrusion cast film line using 2 extruders to feed a Cloeren™ (Cloeren Co., Orange, Tex.) ABA feedblock. The two A layers (first and second skin layers) were extruded with a 2.54 cm diameter single screw extruder (24:1 L/D) manufactured by Killion Extruders (Davis-Standard Corp. Cedar Grove, N.J.). The A layer compositions were blends of Union Carbide 7C12N impact copolymer as a polyolefin base, with Dexco Vector™ 4211 SIS rubber or Engage 8401 ULDPE with the component percentages shown in Table 1 below. Slip and antiblock additives were also incorporated into the skin layers in film samples 30 and 31. The A layers were extruded at 55 RPM and a melt temperature of 218° C. The B layers (the elastomeric core) were extruded with a 6.35 cm diameter single screw extruder (24:1 L/D) manufactured by Davis-Standard (Davis-Standard Corp. Pawcatuck, Conn.). A blend of Dexco Vector™ 4211 SIS rubber (85%) and Huntsman G18 polystyrene (15%) was used for the B layers of film samples 21–34 and was extruded at 80–81 RPM and a melt temperature of 238° C. The 3 layer film was extruded into a nip formed with a rubber roll and a chrome roll.

TABLE 1

| Film Samples | Skin Composition | Total Film Thickness (microns) | Core:Skin Thickness Ratio |
| --- | --- | --- | --- |
| 1 | Fina 3825 PP 100% | 74 | 1.8 |
| 2 | Fina 3825 PP 100% | 72 | 2.4 |
| 3 | Fina 3825 PP 100% | 77 | 2.6 |
| 4 | Fina 3825 PP 100% | 76 | 3.7 |
| 5 | Fina 3825 PP 100% | 80 | 4.6 |
| 6 | Fina 3825 PP 100% | 77 | 7.4 |
| 7 | Fina 3825 PP 100% | 77 | 9.4 |
| 8 | Elvax 3174 EVA 100% | 72 | 1.6 |
| 9 | Elvax 3174 EVA 100% | 73 | 2.1 |
| 10 | Elvax 3174 EVA 100% | 73 | 3.1 |
| 11 | Elvax 3174 EVA 100% | 74 | 5.5 |
| 12 | Elvax 3174 EVA 100% | 73 | 9.3 |
| 13 | 1058 LDPE 100% | 79 | 1.5 |
| 14 | 1058 LDPE 100% | 75 | 1.9 |
| 15 | 1058 LDPE 100% | 77 | 2.9 |
| 16 | 1058 LDPE 100% | 79 | 5.7 |
| 17 | A = Elvax 3174 EVA 100% C = Fina 3825 PP 100% | 75 | 6.5 |
| 18 | A = Elvax 3174 EVA 100% C = Fina 3825 PP 100% | 95 | 5.7 |
| 19 | A = Elvax 3174 EVA 100% C = Fina 3825 PP 100% | 78 | 7.6 |
| 20 | A = Elvax 3174 EVA 100% C = Fina 3825 PP 100% | 70 | 10 |
| 21 | 7C12N PP 100% | 106 | 46 |
| 22 | 7C12N PP 90% V4211 SIS 10% | 107 | 177 |
| 23 | 7C12N PP 80% V4211 SIS 20% | 104 | 37 |
| 24 | 7C12N PP 70% V4211 SIS 30% | 100 | 55 |
| 25 | 7C12N PP 65% V4211 SIS 35% | 108 | 54 |
| 26 | 7C12N PP 60% | 107 | 72 |

TABLE 1-continued

| Film Samples | Skin Composition | Total Film Thickness (microns) | Core:Skin Thickness Ratio |
|---|---|---|---|
| 27 | V4211 SIS 40%<br>7C12N PP 55%<br>V4211 SIS 45% | 109 | 44 |
| 28 | 7C12N PP 50%<br>V4211 SIS 50% | 101 | 71 |
| 29 | 7C12N PP 45%<br>V4211 SIS 55% | 105 | 84 |
| 30 | 7C12N PP 38%<br>V4211 SIS 58% | 105 | 93 |
| 31 | RS62896 Slip 4%<br>7C12N PP 38%<br>V4211 SIS 58% | 111 | 79 |
| 32 | G200 Antiblock 4%<br>7C12N PP 40%<br>E8401 ULDPE 60% | 105 | 32 |

Materials

Fina 3825 homopolymer polypropylene 30 MFI, 0.900 density, available from Fina Oil & Chemical Co. Dallas, Tex.

Shell Kraton™ G1657 styrene-ethylene/butylene-styrene block copolymer rubber, 8.0 MFI, 0.900 density, available from Shell Chemical Co. Houston, Tex.

DuPont Elvax™ 3174 polyethylene-co-vinylacetate 8.0 MI, 18% VA, 0.941 density, available from E. I. DuPont Wilmington, Del.

Huntsman 1058 low density polyethylene 5.5 MI, 0.922 density, available from Huntsman Chemical Corp. Chesapeake, Va.

Dexco Vector™ 4111 styrene-isoprene-styrene block copolymer rubber, 12 MFI, 0.930 density, available from Dexco Polymers Houston, Tex.

Huntsman 11S12A polypropylene homopolymer, 12 MFI, 0.900 density, available from Huntsman Polypropylene Corp. Woodbury, N.J.

Techmer 1642E4 low density polyethylene/$TiO_2$ concentrate, 50% $TiO_2$, 2.59 density, available from Techmer PM Rancho Dominguez, Calif.

7C12N PP/EPR impact copolymer 20 MFI, 0.900 density, available from Union Carbide Corp. Danbury, Conn.

Dexco Vector™ 4211 styrene-isoprene-styrene block copolymer rubber, 13 MFI, 0.940 density, available from Dexco Polymers Houston, Tex.

DuPont-Dow Engage™ 8401 ULDPE ethylene-octene copolymer, 30 MI, 0.885 density, available from DuPont-Dow Elastomers Wilmington, Del.

ReedSpectrum 00062896 polypropylene/erucamide (95:5) slip agent concentrate available from ReedSpectrum Co. Minneapolis, Minn.

Omyalene™ G200 EPR/$CaCO_3$ (20:80) antiblock concentrate available from Omya GmbH, Cologne, Germany.

Huntsman G18 general purpose polystyrene, 18 MFI, 1.05 density, available from Huntsman Chemical Corp. Chesapeake, Va.

Figure 13:
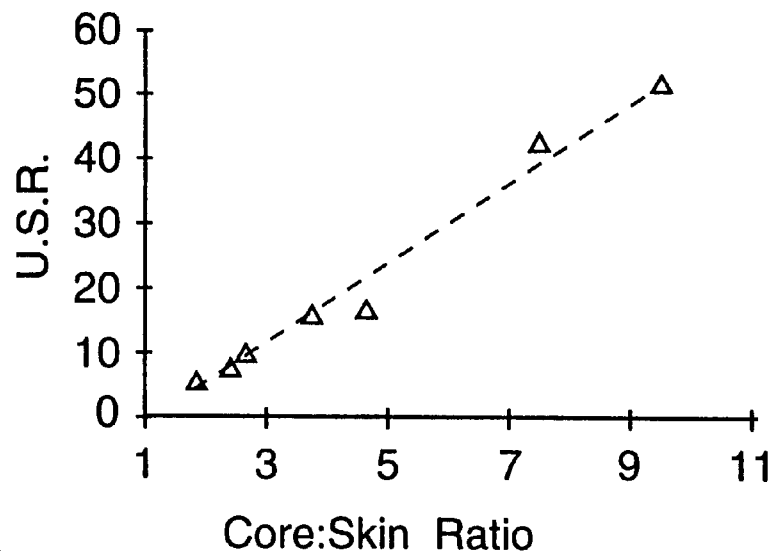
FIG. 13 is a graph of the Useful Stretch Ratios versus the ratio of core layer to skin layer thickness of the coextruded elastic films usable in the invention elastic tab.
Figure 14:
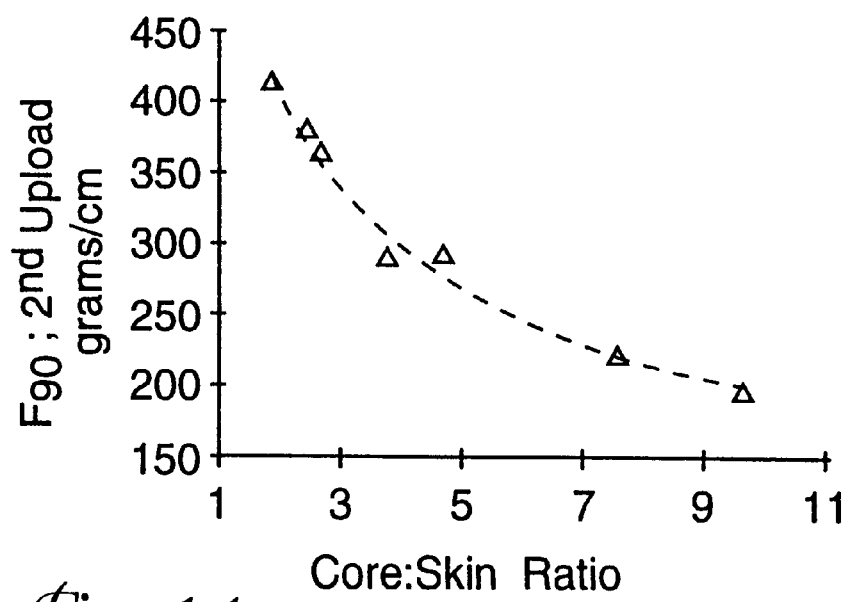
FIG. 14 is a graph of the force versus elongation of a coextruded elastic film usable in the invention laminate which is the force at 90 percent elongation on a second pull.

The effect of Core:Skin Ratio on the Useful Stretch Ratio and $F_{90};2^{nd}$ Upload for a series of film samples using polypropylene as two skin layers is shown in Table 2, and FIGS. 13 and 14, respectively.

TABLE 2

100% ELONGATION TEST

| Film Sample Used | Useful Stretch Ratio (%) | $F_{90}$; $2^{nd}$ Upload (gm/cm) |
|---|---|---|
| 1 | 5.7 | 409 |
| 2 | 7.7 | 377 |
| 3 | 10 | 363 |
| 4 | 16 | 291 |
| 5 | 17 | 293 |
| 6 | 43 | 223 |
| 7 | 52 | 197 |

The effect of Core:Skin Ratio on the Useful Stretch Ratio and $F_{90};2^{nd}$ Upload for a series of film samples using ethylene-co-vinylacetate as two skin layers is shown in Table 3.

TABLE 3

100% ELONGATION TEST

| Film Sample Used | Useful Stretch Ratio (%) | $F_{90}$; $2^{nd}$ Upload (gm/cm) |
|---|---|---|
| 8 | 60 | 179 |
| 9 | 61 | 158 |
| 10 | 73 | 124 |
| 11 | 73 | 128 |
| 12 | 76 | 113 |

The effect of Core:Skin Ratio on the Useful Stretch Ratio and $F_{90}$;2nd Upload for a series of using low density polyethylene as two skin layers is shown in Table 4.

TABLE 4

100% ELONGATION TEST

| Film Sample Used | Useful Stretch Ratio (%) | $F_{90}$; $2^{nd}$ Upload (gm/cm) |
|---|---|---|
| 13 | 59 | 309 |
| 14 | 61 | 281 |
| 15 | 62 | 235 |
| 16 | 70 | 180 |

Figure 12:
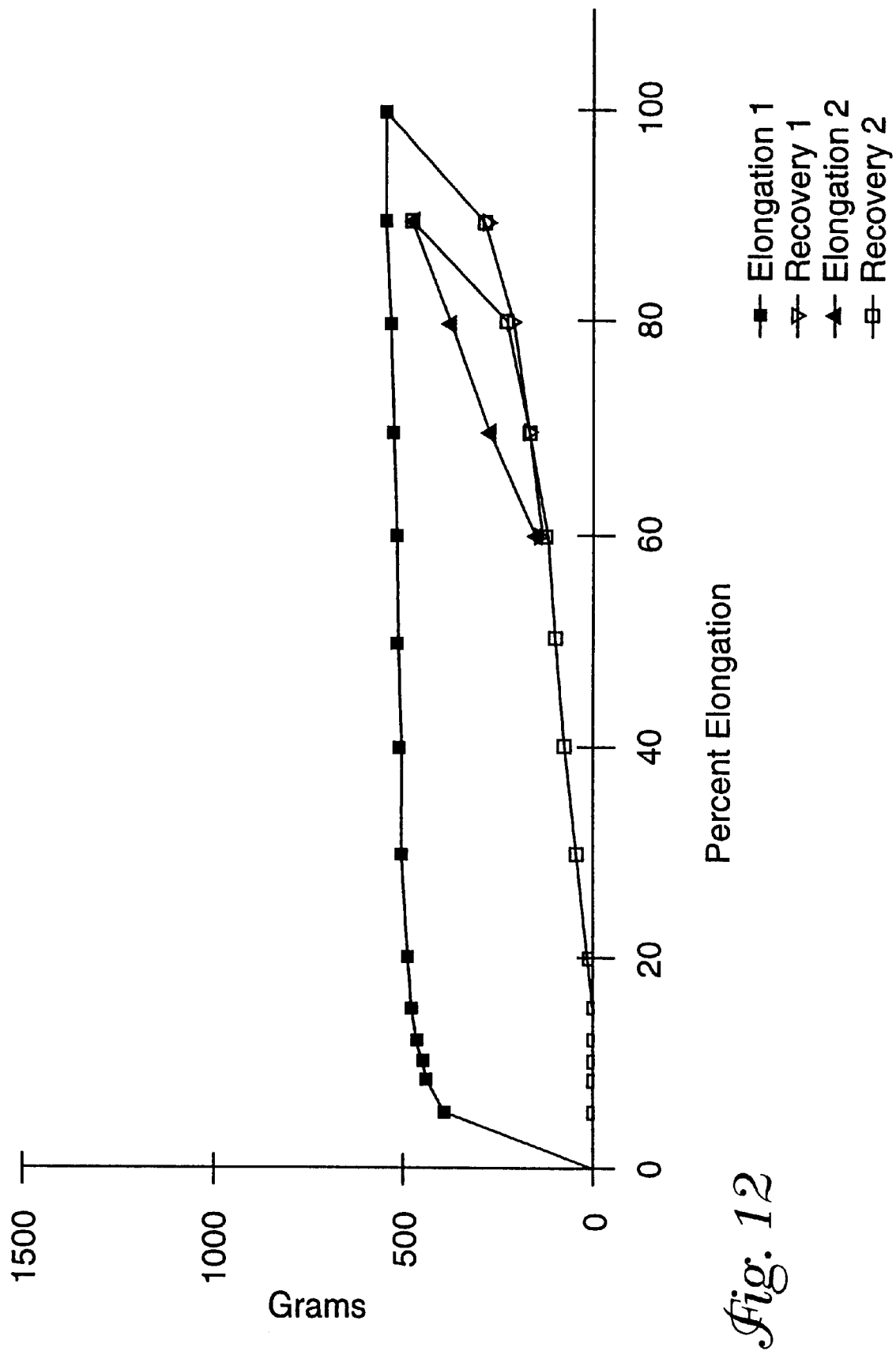
FIG. 12 is a graph of the force versus elongation of a coextruded elastic film usable in the invention laminate.

The effect of Core:Skin Ratio on the Useful Stretch Ratio and $F_{90};2^{nd}$ Upload for a series of film samples using polypropylene as the first skin layer and ethylene-co-vinylacetate as the second skin layer is shown in Table 5. Film sample 20 was additionally tested according to the method described for the Stress $Decay_{70};2^{nd}$ Upload Test except the second elongation (upload) was taken to 90 percent (of the original elongation) rather than 70 percent and the jaw separation rate was 12.7 cm/min. The results are shown in FIG. 12. The second elongation is reflective of the elastic performance during use where the elastic is placed on the user at a set elongation and expands and contracts from that point. The elastic has a relatively narrow range of elastic properties in that range (i.e., a relatively flat stress-strain curve).

TABLE 5

100% ELONGATION TEST

| Film Sample Used | Useful Stretch Ratio (%) | $F_{90}$; $2^{nd}$ Upload (gm/cm) |
|---|---|---|
| 17 | 53 | 254 |
| 18 | 45 | 277 |
| 19 | 53 | 235 |
| 20 | 66 | 219 |

Film samples 1–20 were tested as in Tables 2–5 except an elongation of 400% (10.16 cm) was used. The effect of Core:Skin Thickness Ratio on the Useful Stretch Ratio and $F_{90}$;$2^{nd}$ Upload are shown in Table 6.

TABLE 6

400% ELONGATION TEST

| Film Sample Used | Useful Stretch Ratio (%) | $F_{90}$; $2^{nd}$ Upload (gm/cm) |
|---|---|---|
| 1 | 0.0 | 389 |
| 2 | 0.4 | 398 |
| 3 | 1.9 | 431 |
| 4 | 52 | 379 |
| 5 | 58 | 394 |
| 6 | 70 | 307 |
| 7 | 75 | 271 |
| 8 | 47 | 241 |
| 9 | 53 | 224 |
| 10 | 66 | 252 |
| 11 | 77 | 182 |
| 12 | 82 | 175 |
| 13 | 35 | 351 |
| 14 | 45 | 323 |
| 15 | 65 | 344 |
| 16 | 76 | 227 |
| 17 | 42 | 343 |
| 18 | 39 | 411 |
| 19 | 50 | 380 |
| 20 | 54 | 336 |

Film samples 3, 4, 5, 7, 8, 15, 19 and 25 were tested as in Tables 2–6 except an elongation of 200% (10.16 cm) was used. The effects of skin composition and Core:Skin Thickness Ratio on Useful Stretch Ratio and $F_{90}$;$2^{nd}$ Upload are shown in Table 7.

TABLE 7

200% ELONGATION TEST

| Film Sample Used | Useful Stretch Ratio (%) | $F_{90}$; $2^{nd}$ Upload (gm/cm) |
|---|---|---|
| 4 | 26 | 316 |
| 5 | 43 | 324 |
| 7 | 67 | 217 |
| 8 | 44 | 193 |
| 15 | 44 | 248 |
| 19 | 44 | 278 |
| 25 | 90 | 158 |

Film samples 21, 23, 25, 27, 29, and 32 were tested as in Tables 2;14 5 using an elongation of 100% (2.54 cm). The effect of skin composition at relatively high Core:Skin Thickness Ratios on Useful Stretch Ratio and $F_{90}$;2nd Upload are shown in Table 8.

TABLE 8

100% ELONGATION TEST

| Film Sample Used | Useful Stretch Ratio (%) | $F_{90}$; $2^{nd}$ Upload (gm/cm) |
|---|---|---|
| 21 | 83 | 123 |
| 23 | 84 | 135 |
| 25 | 86 | 130 |
| 27 | 85 | 125 |
| 29 | 86 | 109 |
| 32 | 84 | 109 |

Film samples 1–5 and 21–34 were tested for their Stress Decay$_{250}$;$1^{st}$ Upload properties using an elongation of 250% (6.35 cm). Unwind Force was measured on film samples 21–32 in roll form. The effects of skin composition and Core:Skin Thickness Ratio on Stress Decay$_{250}$;$1^{st}$ Upload and Unwind Force are shown in Table 9.

TABLE 9

250% ELONGATION TEST

| Film Sample Used | Stress Decay$_{250}$; $1^{st}$ Upload (%) | Unwind Force (gm/cm) |
|---|---|---|
| 1 | 58 | — |
| 2 | 59 | — |
| 3 | 59 | — |
| 4 | 53 | — |
| 5 | 49 | — |
| 21 | 23 | 0.9 |
| 22 | 23 | 1.2 |
| 23 | 21 | 1.0 |
| 24 | 20 | 0.9 |
| 25 | 19 | 1.2 |
| 26 | 19 | 1.5 |
| 27 | 18 | 2.6 |
| 28 | 18 | 3.7 |
| 29 | 16 | 26 |
| 30 | 15 | 6.6 |
| 31 | 16 | 22 |
| 32 | 16 | 11 |

Film samples 3, 23, 24, and 26 were tested for their Stress Decay$_{70}$;2nd Upload properties as in Table 9 except the decay was measured on the $2^{nd}$ upload curve as test methods as Stress Decay$_{70}$;$2^{nd}$ Upload. The Stress Decay$_{250}$;$1^{st}$ Upload properties are included for comparison.

TABLE 10

| Film Sample Used | Stress Decay$_{70}$; $2^{nd}$ Upload (%) | Stress Decay$_{250}$; $1^{st}$ Upload (%) |
|---|---|---|
| 3 | 50 | 59 |
| 20 | 26 | 42 |
| 23 | 11 | 21 |
| 24 | 10 | 20 |
| 26 | 10 | 19 |

EXAMPLE 1

A zone corrugated nonwoven/elastic film laminate was prepared using a thermal bonding process. Film sample 20, described in Table 1, was laminated to a 34 grams/meter$^2$ polypropylene spunbond nonwoven manufactured by Avgol Ltd Nonwoven Industries of Holon, Israel (distributed by John Cleaver & Assoc. Wayne, Pa.). The nonwoven was corrugated in-line immediately prior to lamination in a nip formed by upper (116° C.) and lower (149° C.) corrugating steel rolls machined with circumferential ridges spaced across the roll face. The ridges were spaced to provide 2.54 cm wide zones of corrugated nonwoven separated by 5.08 cm wide zones of non-corrugated nonwoven. The corrugating rolls were set such that the circumferential ridges of the upper roll intermeshed with the circumferential ridges of the lower roll. The amount of intermeshing was adjusted as to provide nonwoven loops with about 100% available elongation. The corrugated nonwoven and film sample 20 were fed into a nip formed by the lower corrugating roll (149° C.) and a smooth steel roll (99° C.) and laminated together using a nip pressure of 150 Newtons, resulting in a laminate having nonwoven loops of about 1 mm in height, film/nonwoven bond sites of about 0.07 mm in width, and about 4 loops/cm in the corrugation zones. Useful Stretch Ratio and $F_{90};2^{nd}$ Upload were measured for the resulting nonwoven/elastic film laminate using a 100% elongation test and are reported in Table 11. Properties for film samples 1 and 20 are also included for comparison.

TABLE 11

|  | Useful Stretch Ratio (%) | $F_{90}; 2^{nd}$ Upload (gm/cm) |
| --- | --- | --- |
| Film Sample 1 | 5.7 | 409 |
| Film Sample 20 | 66 | 219 |
| Example 1 | 64 | 246 |

We claim:

1. An extensible elastic tab comprising a coextruded extensible elastic film comprising at least one elastic layer and at least one second layer on at least a first face of the elastic layer, the coextruded elastic film is attached to at least a partially extensible nonwoven layer on at least one face the partially extensible nonwoven layer having a first direction and a second direction the partially extensible nonwoven layer having at least one first portion being extensible in the first direction to an extension limit and at least one second inextensible portion in the first direction, wherein the coextruded elastic and the nonwoven layer when stretched to the extension limit of the nonwoven layer first portion(s) in the first direction will elastically recover at least 1.0 cm, providing an elastic tab having a Useful Stretch Ratio (USR) of at least 30 percent, wherein the USR defined as the ratio of the useful range of elasticity to the initial extension length of the first portion at the upper extension limit, wherein the useful range of elasticity includes the portion of the elastic recovery length having an elastic recovery force of greater than 20 grams/cm force up to the upper extension limit where the upper extension limit is where the extensible elastic tab has an incremental extension force of about 300 grams/cm to 350 grams/cm.

2. The extensible elastic tab of claim 1 wherein coextruded elastic film second layer is an inelastic material or blend.

3. The extensible elastic tab of claim 2 wherein the second layer inelastically deforms in the first direction when extended in the region connected to the first portion of the nonwoven layer.

4. The extensible elastic tab of claim 1 wherein the coextruded film second layer is provided on both faces of the at least one elastic layer.

5. The extensible elastic tab of claim 1 wherein the ratio of the first layer thickness to the second layer thickness is greater than 1.5.

6. The extensible elastic tab of claim 1 wherein the ratio of the first layer thickness to the second layer thickness is from 5 to 1000.

7. The extensible elastic tab of claim 1 wherein the coextruded elastic film has a total thickness of from 25 to 200 microns.

8. The extensible elastic tab of claim 1 wherein the nonwoven layer is attached to only a portion of the coextruded elastic film.

9. The extensible elastic tab of claim 1 wherein the nonwoven layer is coextensive with the coextruded elastic film.

10. The extensible elastic tab of claim 1 wherein the nonwoven layer at least one first portion extends by at least 30 percent.

11. The extensible elastic tab of claim 1 wherein the nonwoven layer at least one first portion extends by at least 75 percent.

12. The extensible elastic tab of claim 11 wherein the nonwoven layer at least one first portion extends from 50 to 400 percent.

13. The extensible elastic tab of claim 11 wherein the nonwoven at least one first portion extends from 75 to 200 percent.

14. The extensible elastic tab of claim 10 wherein the nonwoven layer at least one first portion is attached to the coextruded elastic film at spaced apart bond sites with the nonwoven layer gathered between the bond sites.

15. The extensible elastic tab of claim 14 wherein the spaced apart bond sites are point bond sites.

16. The extensible elastic tab of claim 14 wherein the spaced apart bond sites are linear bond sites.

17. The extensible elastic tab of claim 16 wherein the linear bond sites are substantially parallel.

18. The extensible elastic tab of claim 16 wherein the linear bond sites are substantially equally spaced in the first direction.

19. The extensible elastic tab of claim 16 wherein the linear bond sites are randomly spaced in the first direction.

20. The extensible elastic tab of claim 14 wherein the spaced apart bond sites are nonlinear bond lines.

21. The extensible elastic tab of claim 20 wherein the nonlinear bond lines intersect.

22. The extensible elastic tab of claim 20 wherein the nonlinear bond lines do not intersect.

23. The extensible elastic tab of claim 21 wherein the nonlinear bond lines form a regular geometric pattern.

24. The extensible elastic tab of claim 23 wherein the nonbonded portions of the nonwoven layer between the bond lines are of substantially uniform length dimensions in the first direction.

25. The extensible elastic tab of claim 20 wherein the nonlinear bond lines are created by compacting the nonwoven layer in the first direction.

26. The extensible elastic tab of claim 1 wherein the nonwoven layer at least one first portion attached to the coextruded elastic film and has a plurality of slits provided which allow the nonwoven layer to be extended in the first direction.

27. The extensible elastic tab of claim 26 wherein the plurality of slits are substantially parallel and the nonwoven layer at least one first portion and the coextruded elastic film are substantially coplanar.

28. The extensible elastic tab of claim 1 wherein the coextruded elastic film is thermally bonded to the nonwoven layer.

29. The extensible elastic tab of claim 1 wherein the coextruded elastic film is adhesively bonded to the nonwoven layer.

30. The extensible elastic tab of claim 1 wherein the nonwoven layer second inextensible portion length in the second direction is substantially equal to the length of the coextruded elastic film to which it is attached.

31. The extensible elastic tab of claim 1 wherein the second inextensible portion is substantially coplanar with the coextruded elastic film in the first direction.

32. The extensible elastic tab of claim 31 wherein the second inextensible portion is substantially planer with the coextruded elastic film in the second direction.

33. The extensible elastic tab of claim 1 wherein the nonwoven layer is a substantially inextensible nonwoven having an initial yield force of at least 100 gm/cm.

34. The extensible elastic tab of claim 1 wherein the extensible tab has a fastening element on at least one fastening portion the fastening portion forming at least a part of the extensible elastic tab having the nonwoven layer second inextensible portion.

35. The extensible elastic tab of claim 34 wherein the fastening element comprises an adhesive layer.

36. The extensible elastic tab of claim 34 wherein the fastening element comprises a mechanical fastening element.

37. The extensible elastic tab of claim 34 wherein the fastening element is attached to the second face of the coextruded elastic film.

38. The extensible elastic tab of claim 34 wherein the fastening element is directly adhered to the coextruded elastic film first face.

39. The extensible elastic tab of claim 34 wherein different fastening elements are attached to different fastening portions.

40. The extensible elastic tab of claim 36 wherein the mechanical fastening element is a hook mechanical fastening element.

41. The extensible elastic tab of claim 40 wherein the mechanical fastening element is a loop mechanical fastening element.

42. The extensible elastic tab of claim 33 wherein the nonwoven layer comprises a fibrous web wherein the fibers are mutually bond to each other at points of intersection.

43. The extensible elastic tab of claim 33 wherein the nonwoven layer comprises a spunbond web.

44. The extensible elastic tab of claim 1 wherein the extensible elastic tab will elastically recover from 2.0 to 7.0 cm.

45. The extensible elastic tab of claim 1 wherein the extensible elastic tab will have a Useful Stretch Ratio of greater than 40 percent.

46. The extensible elastic tab of claim 1 wherein the second inextensible portion will not extend when placed under a force of 300 grams/cm or less.

47. The extensible elastic tab of claim 1 wherein the extensible elastic tab will have a Useful Stretch Ratio portion and a second inextensible portion which inextensible portion will not extend when placed under a force of 400 grams/cm or less.

48. The extensible elastic tab of claim 1 wherein the extensible portion of the tab has a width of from 1 to 10 cm.

49. The extensible elastic tab of claim 1 wherein the incremental force increase required to further stretch the extensible portion of the tab beyond its extension limit is at least 100 grams/cm.

50. The extensible elastic tab of claim 1 wherein the incremental force increase required to further stretch the extensible portion of the tab beyond its extension limit is at least 200 grams/cm.

51. The extensible elastic tab of claim 2 wherein the second layer comprises a blend of a thermoplastic elastomer and an inelastic polymer.

52. The extensible elastic tab of claim 51 wherein the thermoplastic elastomer comprises 0 to 70 percent by weight of the second layer.

53. The extensible elastic tab of claim 51 wherein the thermoplastic elastomer comprises 5 to 50 percent by weight of the second layer.

* * * * *

UNITED STATES PATENT AND TRADEMARK OFFICE
CERTIFICATE OF CORRECTION

PATENT NO.   : 6,159,584
DATED        : December 12, 2000
INVENTOR(S)  : Eaton, Bradley W.

It is certified that error appears in the above-identified patent and that said Letters Patent is hereby corrected as shown below:

Column 8,
Line 12, delete "through" and insert in place thereof -- through --.

Column 12,
Line 34, delete "sldn" and insert in place thereof -- in --.

Column 14,
Line 24, delete "sldn" and insert in place thereof -- skin --.

Column 15,
Line 25, delete "sldn" and insert in place thereof -- in --.
Line 33, delete "(32:1 LED)" and insert in place thereof -- 2:1 L/D ) --.
Line 34, delete "Kraton" and insert in place thereof -- Kraton$^{TM}$ --.

Column 19,
Line 64, delete "2;14 5" and insert in place thereof -- 2-5 --.

Column 20,
Line 46, insert -- described in the -- following "as" and preceding "test".

Column 22,
Line 22, delete "200" and insert in place thereof -- 400 --.

Signed and Sealed this

Fifth Day of August, 2003

JAMES E. ROGAN
*Director of the United States Patent and Trademark Office*